US008681939B2

(12) United States Patent
Karev et al.

(10) Patent No.: US 8,681,939 B2
(45) Date of Patent: **\*Mar. 25, 2014**

(54) DEVICE FOR DETECTION AND IDENTIFICATION OF CARBON- AND NITROGEN-CONTAINING MATERIALS

(75) Inventors: Alexander Ivanovich Karev, Moscow (RU); Valery Georgievich Raevsky, Moscow (RU); Leonid Zavenovich Dzhilavyan, Moscow (RU); Valery Dmitrievich Laptev, Troitsk (RU); Nikolay Ivanovich Pakhomov, Moscow (RU); Vasily Ivanovich Shvedunov, Moscow (RU); Vladimir Ivanovich Rykalin, Protvino (RU); Louis Joseph Brothers, Union, KY (US); Larry K. Wilhide, Newville, PA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 79 days.

This patent is subject to a terminal disclaimer.

(21) Appl. No.: 13/253,934

(22) Filed: Oct. 5, 2011

(65) Prior Publication Data

US 2012/0138794 A1 Jun. 7, 2012

Related U.S. Application Data

(60) Provisional application No. 61/534,177, filed on Sep. 13, 2011, provisional application No. 61/534,219, filed on Sep. 13, 2011.

(30) Foreign Application Priority Data

Dec. 6, 2010 (RU) ................................ 2010149620
Dec. 6, 2010 (RU) ................................ 2010149621

(51) Int. Cl.
*G01N 23/22* (2006.01)

(52) U.S. Cl.
USPC ........ 378/88; 378/119; 378/98.8; 250/370.09

(58) Field of Classification Search
USPC ......... 378/64, 65, 98.8, 98.9, 120, 57, 86–88, 378/119; 250/370.09
See application file for complete search history.

(56) References Cited

U.S. PATENT DOCUMENTS 3,832,545 A * 8/1974 Bartko ........................... 376/159
3,959,687 A * 5/1976 Schriber ...................... 315/5.42

(Continued)

FOREIGN PATENT DOCUMENTS

| KR | 10-0261746 | 1/2000 |
| RU | 2185614 | 7/2002 |
| RU | 2226686 | 4/2004 |

OTHER PUBLICATIONS

Trower et al., Nitrogen Camera: Detection of Anti-Personnel Mines, SPIE vol. 2933, 58-66.*
Shvedunov et al., "70 MEV Electron Racetrack Microtron Commissioning," Proceedings of the 2001 Particle Accelerator Conference, Chicago, 2596-2598.*
Trower, W.P., et al., Imaging Carbon and Nitrogen Concentrations and the Interdiction of Concealed Narcotics and Explosives, Virginia Journal of Science 1993, 44: 293-300.

(Continued)

*Primary Examiner* — Allen C. Ho
(74) *Attorney, Agent, or Firm* — Steinfl & Bruno, LLP

(57) ABSTRACT

A device for detection and identification of carbon- and nitrogen-containing materials is described. In particular, the device performs the detection and identification of carbon- and nitrogen-containing materials by photo-nuclear detection. The device may comprise a race-track microtron, a breaking target, and a water-filled Cherenkov radiation counter.

18 Claims, 8 Drawing Sheets

(56) References Cited

U.S. PATENT DOCUMENTS

| | | | |
|---|---|---|---|
| 4,123,720 A * | 10/1978 | Rosander et al. | 315/505 |
| 4,200,844 A * | 4/1980 | Nunan | 315/505 |
| 4,389,568 A * | 6/1983 | Dowdy et al. | 250/362 |
| 4,453,079 A * | 6/1984 | Woodbridge | 250/432 R |
| 4,623,847 A * | 11/1986 | Anderberg et al. | 315/505 |
| 4,726,046 A * | 2/1988 | Nunan | 378/65 |
| 4,756,866 A | 7/1988 | Alvarez | |
| 4,843,333 A * | 6/1989 | Marsing et al. | 315/503 |
| 4,980,901 A | 12/1990 | Miller | |
| 5,115,459 A | 5/1992 | Bertozzi | |
| 5,477,056 A * | 12/1995 | Hirota et al. | 250/492.2 |
| 5,851,182 A * | 12/1998 | Sahadevan | 600/407 |
| 6,552,347 B1 * | 4/2003 | Dimcovski | 250/363.01 |
| 6,559,610 B2 * | 5/2003 | Tanaka | 315/506 |
| 7,601,965 B1 * | 10/2009 | Bell et al. | 250/390.11 |
| 7,629,588 B1 * | 12/2009 | Bell et al. | 250/390.11 |
| 7,683,335 B2 * | 3/2010 | Treadwell et al. | 250/368 |
| 7,826,593 B2 * | 11/2010 | Svensson et al. | 378/65 |
| 7,902,530 B1 * | 3/2011 | Sahadevan | 250/494.1 |
| 8,373,133 B2 * | 2/2013 | Dazeley et al. | 250/366 |
| 8,457,274 B2 * | 6/2013 | Arodzero et al. | 378/57 |
| 2002/0169351 A1 | 11/2002 | Brown | |
| 2008/0156997 A1 | 7/2008 | Kearfott | |

OTHER PUBLICATIONS

Karev, A.I., et al., The High Efficiency Complex for Detection of Landmines, Detection of Explosives and Landmines 2002, 185-193.

Knapp, E.A., et al., Direct Imaging of Explosives, Applied Radiation and Isotopes 2000, 53: 711-716.

PCT International Search Report mailed on May 14, 2012 for PCT Application No. PCT/US2011/054996 filed on Oct. 5, 2011 in the name of Lawrence Livermore National Security, LLC et al.

PCT Written Opinion mailed on May 14, 2012 for PCT Application No. PCT/US2011/054996 filed on Oct. 5, 2011 in the name of Lawrence Livermore National Security, LLC et al.

PCT International Search Report mailed on May 14, 2012 for PCT Application No. PCT/US2011/054998 filed on Oct. 5, 2011 in the name of Lawrence Livermore National Security, LLC et al.

PCT Written Opinion mailed on May 14, 2012 for PCT Application No. PCT/US2011/054998 filed on Oct. 5, 2011 in the name of Lawrence Livermore National Security, LLC et al.

Non-Final Office Action mailed on Oct. 17, 2012 for U.S. Appl. No. 13/253,927 filed on Oct. 5, 2011 in the name of Alexander Ivanovich Karev et al.

Final Office Action mailed on Mar. 22, 2013 for U.S. Appl. No. 13/253,927 filed Oct. 5, 2011 in the name of Alexander Ivanovich Karev et al.

* cited by examiner

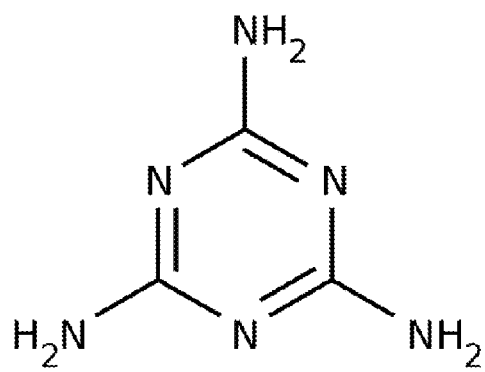# 
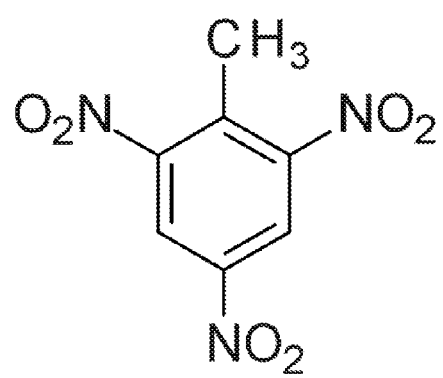
*FIG. 6A*     *FIG. 6B*

DEVICE FOR DETECTION AND IDENTIFICATION OF CARBON- AND NITROGEN-CONTAINING MATERIALS

CROSS REFERENCE TO RELATED APPLICATIONS

The present application claims priority to Russian Application No. 2010149621, filed on Dec. 6, 2010, Russian Application No. 2010149620, filed on Dec. 6, 2010, U.S. Provisional Application 61/534,177, filed on Sep. 13, 2011, and U.S. Provisional Application 61/534,219, filed on Sep. 13, 2011, all of which are incorporated herein by reference in their entirety. The present application is also related to U.S. patent application Ser. No. 13/253,927 published as US. Pub. No. 2012/0140863 A1, entitled "Methods of Detection and Identification of Carbon-and Nitrogen-Containing Materials", and filed on even date herewith, the disclosure of which is attached hereto as Annex A.

STATEMENT OF GOVERNMENT GRANT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD

The present disclosure relates to a device for detection and identification of carbon- and nitrogen-containing materials. In particular, it relates to a device for detection and identification of concealed carbon- and/or nitrogen-containing materials by photo-nuclear detection.

SUMMARY

According to a first aspect, a device is described comprising: an electron accelerator configured to generate pulses of an accelerated electron beam; a breaking target configured to receive the pulses of the accelerated electron beam and generating an incident gamma radiation to be directed at a test object; and a radiation detector configured to detect and measure secondary gamma radiation from carbon- and/or nitrogen-containing materials in the test object undergoing radioactive decay following irradiation of the test object by the incident gamma radiation, thus detecting and identifying the carbon- and/or nitrogen-containing materials in the test object.

According to a second aspect of the disclosure, a device is described comprising: an electron accelerator, comprising a race-track microtron with an operating energy of >50 MeV and configured to generate pulses of an accelerated electron beam; a bremsstrahlung target (i.e. a braking target), comprising tantalum and configured to receive the pulses of the accelerated electron beam and generating an incident gamma radiation to be directed at a test object; and a radiation detector, comprising a water-filled Cherenkov radiation counter and configured to detect and measure secondary gamma radiation from carbon and/or nitrogen materials undergoing radioactive decay following irradiation of the test object by the incident gamma radiation, thus detecting and identifying the carbon and/or nitrogen containing materials in the test object.

Further embodiments of the present disclosure can be found in the written specification, drawings, and claims of the present application. According to some embodiments of the present disclosure, a device for detection and identification of carbon- and/or nitrogen-containing materials such as concealed explosive materials and narcotic substances and methods for use of said device are described.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 6 shows chemical structures for melamine (FIG. 6A) and trinitrotoluene (FIG. 6B).

DETAILED DESCRIPTION

Figure 1:
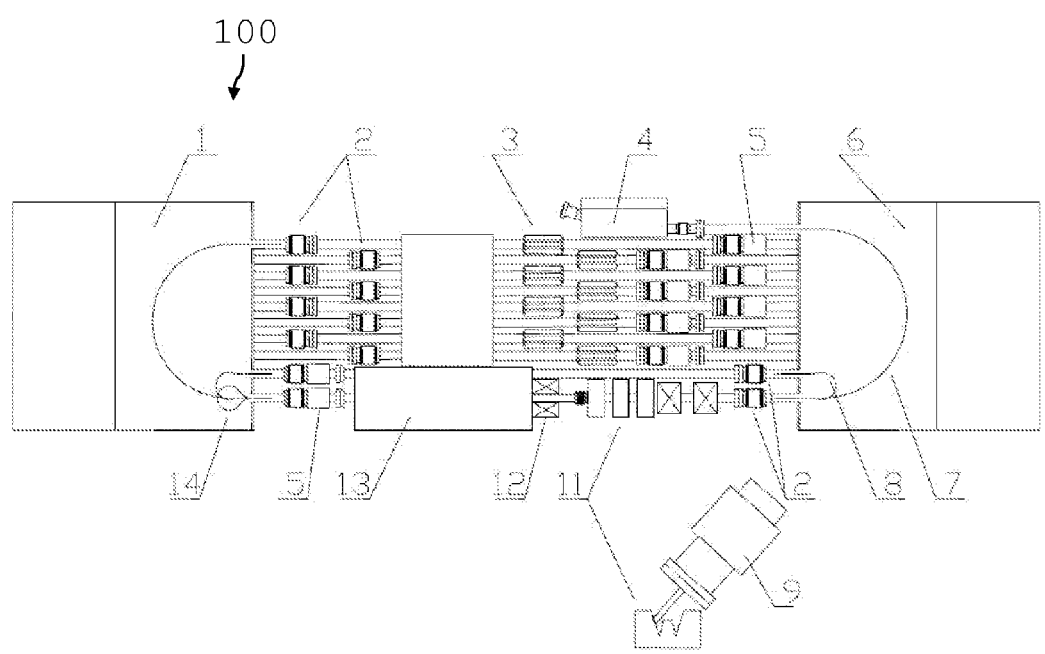
FIG. 1 shows a schematic of an exemplary race-track microtron (100) according to an embodiment of the present disclosure.

The present disclosure relates to the field of discovering concealed explosive materials and narcotic substances by a method of photo-nuclear detection, and may be used in stationary or mobile installations—for example, but not limited to screening baggage of air passengers, cargo containers, mail, or vehicles, such as trucks at border crossings; performing inspections at customs or guard posts; or clearing of landmines from areas within a framework of humanitarian activities, etc.

The proposed device makes possible the detection of concealed explosives and narcotics by irradiating a targeted object with a beam of gamma radiation generated by a 55-MeV electron beam from a race-track microtron, followed by an analysis of secondary gamma radiation from the targeted object, as registered by a water-filled Cherenkov radiation counter. The technical result of the proposed device is an increase in operating speed and sensitivity, and a decrease in likelihood of false positives in a search for concealed explosives and narcotics.

The device of the present disclosure may be utilized to detect hidden explosives and narcotics by using a method based on a photo-nuclear technique which identifies a concealed substance by its content of nitrogen and/or carbon, which are the chemical elements that form the basis of modern explosives and natural narcotics. Aspects of the photo-nuclear method have been proposed in Reference [1] and developed in References [2-5]. The References [1-5] are incorporated herein by reference in their entirety.

The photo-nuclear method can be described as follows:

If an object under inspection contains nitrogen and/or carbon atoms and is irradiated by a beam of gamma radiation of sufficiently high energy, then the following photonuclear reactions may take place within the object:

$$\gamma + {}^{14}N \to {}^{12}B + p + p \to {}^{12}C + e^- + v_e (T_{1/2} \cong 20.2 \text{ ms})$$
$$(E_{\gamma t} \cong 25.1 \text{ MeV}) \quad (1)$$

$$\gamma + {}^{14}N \to {}^{12}N + n + n \to {}^{12}C + e^+ + v_e (T_{1/2} \cong 11.0 \text{ ms})$$
$$(E_{\gamma t} \cong 30.6 \text{ MeV}) \quad (2)$$

$$\gamma + {}^{13}C \to {}^{12}B + p \to {}^{12}C + e^- + v_e (T_{1/2} \cong 20.2)(E_{\gamma t} \cong 17.5 \text{ MeV}) \quad (3)$$

where $E_{\gamma t}$ is the energy threshold for incident gamma radiation of $\gamma$-quanta which may excite and initiate one or more of the reactions shown in equations (1), (2) and (3), and $T_{1/2}$ is the half-life period of each of the resulting radionuclide decay, such as $^{12}B \to {}^{12}C + e^- + v_e$.

The isotopes $^{12}B$ and $^{12}N$, which are formable by the reactions shown in equations (1), (2) and (3), are β-active. The process of decay for isotopes $^{12}B$ and $^{12}N$ emits electrons with a maximum energy of ~13 MeV and positrons with a maximum energy of ~17 MeV respectively. The emitted electrons and positions, upon undergoing braking and decelerating within a substance, in turn can emit secondary γ-quanta. These secondary emitted γ-quanta may be recorded by a detector of gamma radiation. It is thus possible to measure only the time spectrum of events recorded by such a detector of the secondary radiation as an indirect method to detect the initial $^{12}B$ and $^{12}N$ isotopes formed by the incident gamma radiation.

Reactions (1-3) as shown in equations (1), (2) and (3) have a number of unique features which may be utilized for the detection of isotopes $^{12}B$ and $^{12}N$. In particular, the isotopes $^{12}B$ and $^{12}N$ generated by the reactions (1-3) have lifetimes which are short and distinguishable from one other. In addition, the reactions (1-3) can be initiated and terminated by pulses or fluxes of high energy gamma radiation which can penetrate depths beyond a typical surface concealment of several cm thick or more. Therefore, a device based on reactions (1-3) may be utilized for the detection of concealed explosive materials and narcotic substances. The device may have good operating speed, sensitivity, and penetrating capability, and may have a reasonably low probability of encountering false responses according to Reference [5].

The device for the detection of explosives and narcotics as described in the present disclosure may comprise at least two basic components, the two components comprising a pulse generator for generating a primary flux of high-energy incident gamma quanta that irradiate the object being inspected, and a system for registering the secondary gamma radiation.

A previous experimental apparatus for studying a photo-nuclear method of detection, as described in References [2] and [3], can be considered a prototype of the device of the present disclosure. The prototype assembly consists of a 50-MeV microtron, which is a compact recirculating electron accelerator, a bremsstrahlung target, and a system for registering the secondary radiation.

The microtron produces an electron beam with a pulse duration of 5 μsec, a pulse current of 1 mA, and a frequency of 1 Hz which is directed at a tantalum bremsstrahlung target. The irradiated tantalum target generates a beam of gamma radiation which can be used to irradiate an object to be investigated. The object to be investigated forms radionuclides, for example via reactions (1-3), as a result of irradiation by the beam of gamma radiation. The formed radionuclides decay and emit secondary radiation which is registered by four gamma detectors. Each gamma detector consists of cylindrical organic scintillators measuring ~13 cm in diameter and ~6 cm in length, and photomultiplier tube (PMT).

One disadvantage of the prototype experimental apparatus as described in References [2] and [3] is its slow operating speed. In a detection test for substances containing nitrogen and/or carbon, a 300-gram packet of melamine ($C_3N_6H_3$) (see FIG. 6A for chemical structure) required an irradiation dose approximately equal to 1,500 scans, which took about 25 minutes to complete.

Another disadvantage of the prototype experimental apparatus as described in References [2] and [3] is related to its use of organic scintillators for the registration of the secondary radiation. Detectors based on organic scintillators have been widely used in experimental nuclear physics, however, their use for registering secondary radiation in photonuclear detectors of explosives and narcotics has a number of deficiencies. One of such deficiency is due to a large number of photo-neutrons being generated into the bremsstrahlung target with maximum kinetic energies approximately equal to the kinetic energy of electrons from the electron accelerator which is reduced to the energy of a neutron bond.

These photoneutrons can, in turn, activate the carbon in the composition of an organic scintillator. In the presence of sufficiently high energy photoneutrons, carbon can undergo the following the nuclear reaction, which produces the same radionuclides and secondary radiation as the reaction shown in equation (3):

$$n + {}^{12}C \to {}^{12}B + p \to {}^{12}C + e^- + v_e (T_{1/2} \cong 20.2 \text{ ms})(E_n \cong 12.6 \text{ MeV}) \quad (4)$$

The threshold value of the kinetic energy of the photoneutrons required to initiate this reaction is ≅12.6 MeV. This is substantially lower than the kinetic energy of electrons in the 50 MeV beam. Therefore background signals generated by the photoneutrons via a reaction with carbon found in the body of an organic scintillator can be significant and can potentially interfere with the extraction of signals of interest from the nitrogen and carbon in the irradiated object. This increased background signal can hinder the detection process, lead to a decrease in sensitivity of a detector of explosives and narcotics, and increase the probability of false responses.

One other disadvantage of the prototype experimental apparatus as described in References [2] and [3] is due to the use of scintillators in general, both organic and inorganic. When these scintillators are used in conjunction with intense pulsed beams of bremsstrahlung radiation in a medium energy range, it is known in the art that a scintillator measuring secondary gamma radiation may become loaded by background gamma quanta with energy levels of less than 2 MeV, arising from various other electromagnetic processes besides the process or reaction of concern. Therefore, to suppress this background it would be desirable to find a detector of secondary gamma radiation, which has an operating threshold higher than 2 MeV to avoid complications arising from these known sources of background gamma quanta.

In the case of both organic and inorganic scintillators, the background gamma quanta with energy level of less than 2 MeV can be separated by the signal of interest by using threshold discriminators in photomultiplier signal circuits at the expense of additional complications to the structure of the detector, such as signal filtering components. However, using threshold discriminators does not eliminate the accompanying illumination of a photomultiplier's photocathode and may not eliminate a spurious load from superimposed pulses. Therefore, the background gamma quanta described here is another factor which limits the use of scintillators in the detection of explosives and narcotics.

Device for Detecting Photonuclear Reaction

The device described by the present disclosure can be used to improve operating speed and sensitivity, and to decrease the probability of false responses in a search for concealed explosives and narcotics. In an embodiment of the device of the present disclosure, the device may comprise a compact race-track microtron with 55-MeV energy, a bremsstrahlung target, and a system for registering the secondary radiation based on a water-filled Cherenkov counter.

The device of the present disclosure is improved over the experimental apparatus of Reference [2] and [3] in at least the following areas. First, to increase the operating speed for detection of explosives and narcotics, the number of electrons accelerated in one pulse of the microtron—and accordingly the number of gamma quanta which irradiate the object to be scanned in one pulse—is increased by more than 10 times over that of the prototype. Secondly, to increase the sensitivity and decrease the probability of false responses, the device of the present disclosure utilizes a water-filled Cherenkov counter (WCC) for registering the secondary radiation instead of organic or inorganic scintillation counters. The water-filled Cherenkov counter has an inherent registration energy threshold of about 2 MeV. This energy threshold acts as a natural filter and decreases the load from low-energy gamma quanta occurring as a result of various background electromagnetic processes. Additionally, in contrast to the organic scintillation counters used in the prototype experimental apparatus, the structure of a WCC contains no carbon in the body of the counter which can undergo reaction (4) and create background signals potentially interfering with the detection of explosives and narcotics.

Race-Track Microtron

Referring now to FIG. 1, an exemplary race-track microtron (100) according to an embodiment of the present disclosure is shown herein. The race-track microtron (100), also referred to as RTM-55 microtron, may comprise an injection system, an accelerating structure (AS) (13), two reversing end magnets (1 and 6), a radiofrequency (RF) feed system, a vacuum system, a beam diagnostic and steering system, and a control system. A radiofrequency (RF) feed system, a vacuum system, and a control system are further exemplified in FIGS. 7 and 8.

The injection system may comprise a 50-keV tri-electrode electron gun (9), an injector magnet (11) (seen in the lower part of FIG. 1), and a solenoid lens (12).

The accelerating structure (13) may be bi-periodic, comprising 7 accelerating cells and 6 coupling cells, operating in a standing-wave regime with an oscillation mode of $\pi/2$ at a frequency of approximately 2,856 MHz.

Each reversing end magnet (1 and 6) may comprise an electromagnet with a pair of windings and poles that can create a uniform magnetic field with an induction field of about 1 T, a pair of supplemental windings and poles that can create a reverse magnetic field, and active and passive screens at an entrance to the magnet.

Figure 7:
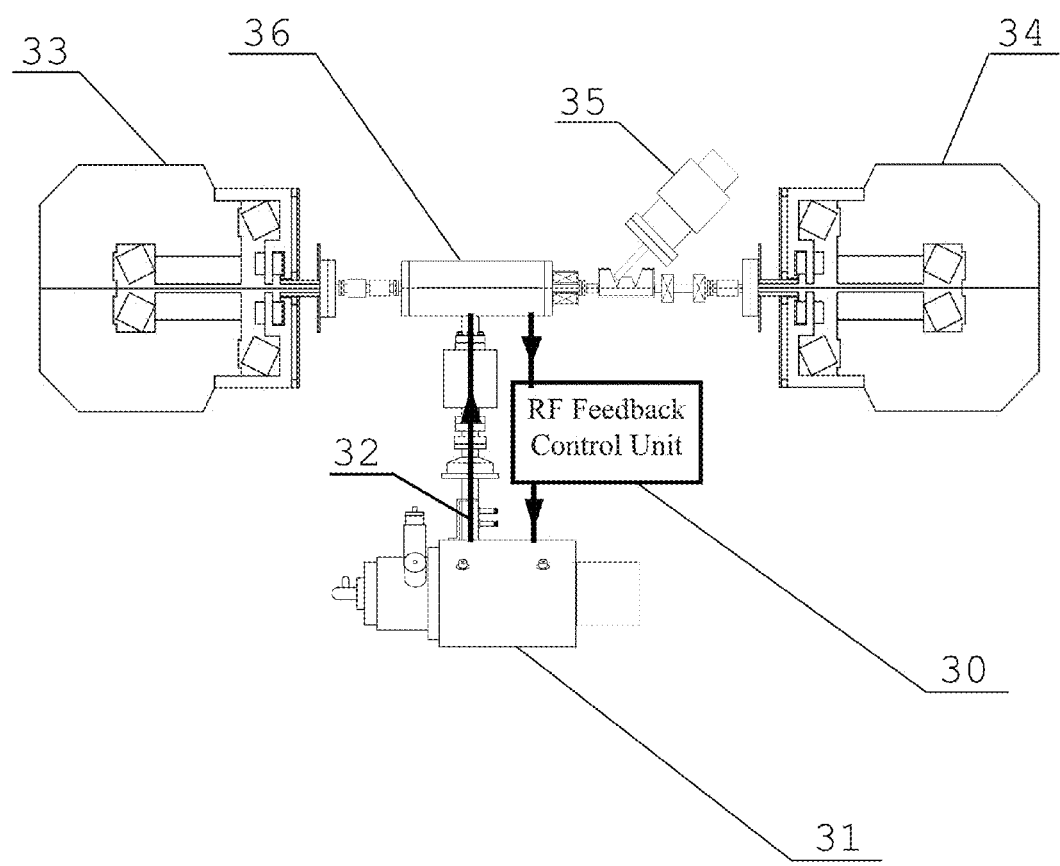
FIG. 7 shows an exemplary RF feed system comprising a klystron (31), an RF feedback control unit (30), a linear particle accelerator (36), two reversing end magnets (33,34), and an electron gun (35).

The RF feed system may comprise a klystron operating in a self-oscillation mode, and a remotely controlled device for a feedback loop. FIG. 7 is exemplary of an RF feed system utilizing high power RF (32) and comprising a klystron (31), a linear particle accelerator (36), two reversing end magnets (33,34), an RF feedback control unit (30) and an electron gun (35).

The vacuum system may comprise two vacuum chambers, mounted between the poles of the end magnets, beam-line tubes with bellows mountings (2), and a central vacuum chamber connected to an ion (i.e. magnetic-discharge) pump.

A beam diagnostic and correction system comprises magnetic-induction beam current monitors (5), steering coils (3) that permit correcting of the beam direction in a drift space between the end magnets, and a monitor for synchrotron radiation which is emitted through a window in the vacuum chamber in an end magnet, and is observed with the aid of a television camera.

Figure 8:
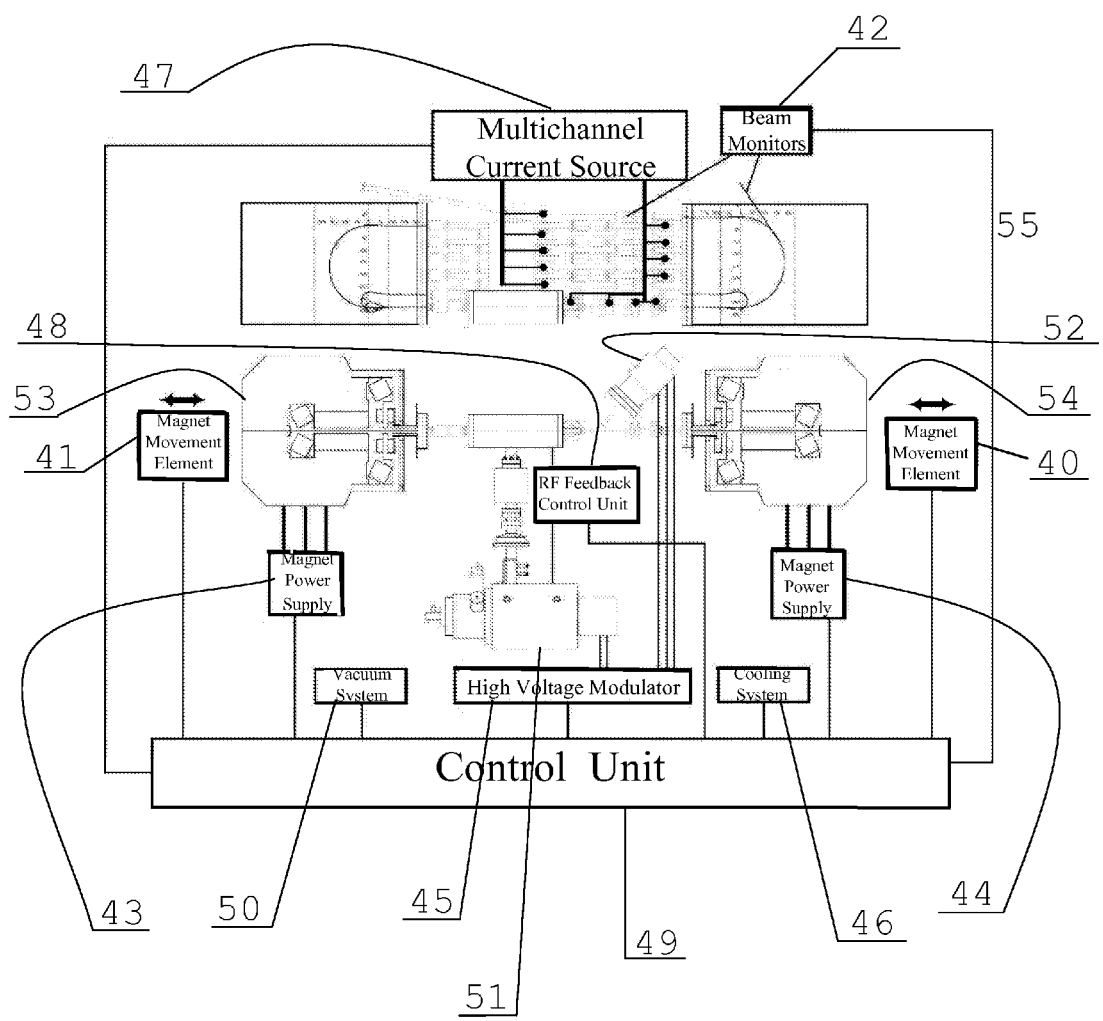
FIG. 8 shows an example of a control system for an electron accelerator based on a variety of sensing elements.

A control system for an electron accelerator according an embodiment of the present disclosure may be based on a variety of sensing elements, for example as shown in FIG. 8, which provides information on dynamics of a beam and functioning of various devices and operating components which permit control of components by means of a computer. FIG. 8, by way of example and not of limitation, shows a control unit (49) that may be adapted to control the following components: beam monitors (42), magnet power supplies (43,44) for reversing end magnets (53,54) as well as magnet movement elements (40,41), a vacuum system (50), a cooling system (46), an RF feedback control unit (48) and klystron (51), a high voltage modulator (45) and electron gun (52), and a multichannel current source (47) for steering coils, quadrupoles, solenoids, and dipole. Control of the above-mentioned components (42-48 and 50-54) by sensing elements is indicated in FIG. 8 by way of lines connecting the operating components to the control unit (49), for example the line (55) connecting the control unit (49) to the beam monitors (42). One skilled in the art would be able to arrive at other embodiments of a control unit without departing from the scope of the present disclosure.

Operation of the race-track microtron (100) may proceed in the following manner. A beam of electrons from the electron gun (9) is injected into the accelerating structure (AS) (13) through the injector magnet (11) and the solenoidal lens (12). After a first passage through the AS, electrons with an energy of roughly 5 MeV are reflected back along the axis of the AS as a result of a special configuration of the magnetic field at the entrance to Magnet (1). If the AS operates in standing-wave mode, the beam, moving in the reverse direction, is accelerated a second time and, acquiring a total energy of 10 MeV, returns to Magnet (6) and begins to circulate in orbit until it has acquired a total energy of 55 MeV. After this, the beam is extracted from the microtron with the aid of Magnet (4) and is directed at the bremsstrahlung target (not shown).

Positions (14), (8), and (7) of FIG. 1 are respectively the trajectories of the accelerated beam after a first, second, and eleventh (last) passage through the accelerating structure (AS).

The basic characteristics of the race-track microtron are given in Table 1.

TABLE 1

| Race-Track Microtron Sample Characteristics | |
|---|---|
| Maximum energy | 55 MeV |
| Pulse output current | up to 50 mA |
| Pulse repetition frequency | 5-50 Hz |
| Number of passes | 11 |
| Energy boost per pass | 5 MeV |
| Pulse current length | up to 16 μsec |
| Operating RF frequency | 2,856 MHz |
| Magnetic field induction of end magnets | 1.0 T |
| Maximum RF power | 5 MW |

Detector

Figure 2:
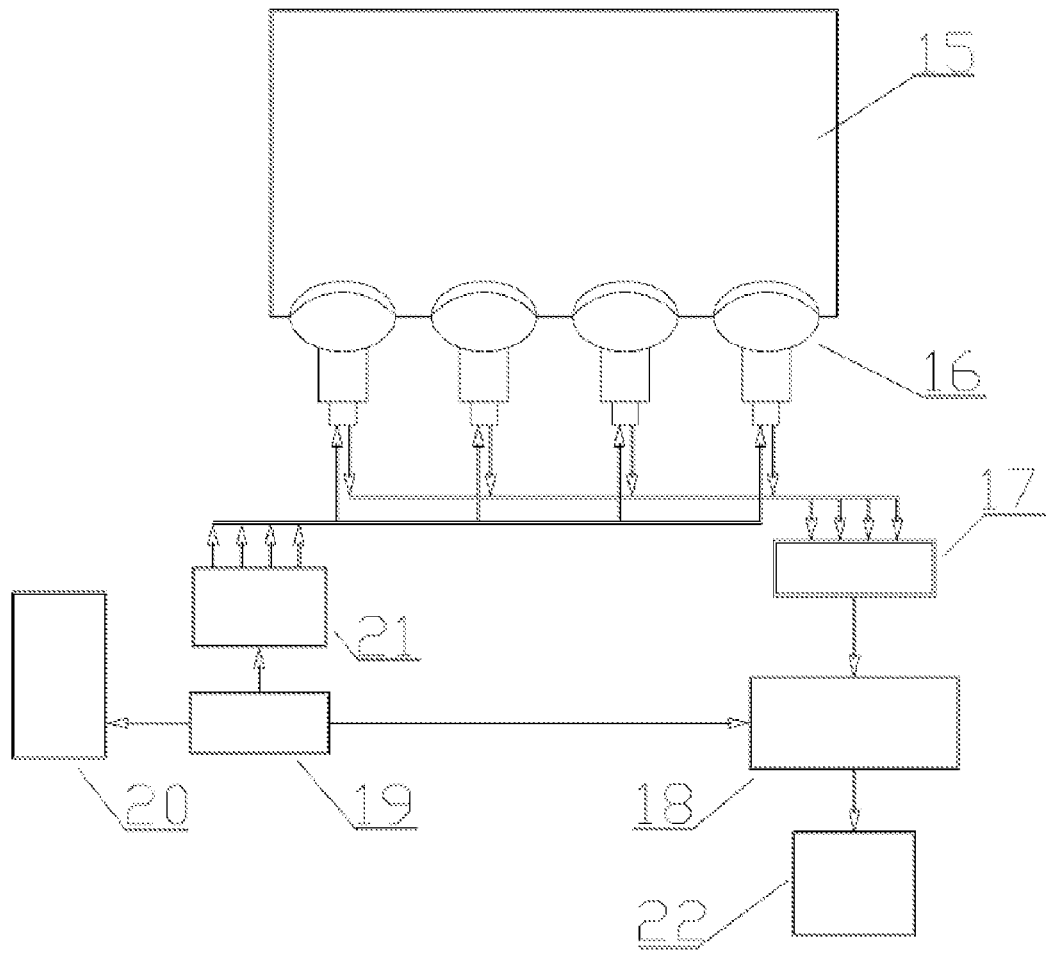
FIG. 2 shows a diagram of a water-filled Cherenkov radiation counter (WCC) and a system for control and registration of signals from the WCC (15).

The device of the present disclosure comprises a system for registering the secondary radiation based on a water-filled Cherenkov counter (WCC) (15) which is used as a detector of the secondary radiation. FIG. 2 shows a diagram of the WCC and a system for control and registration of signals from the WCC (15). The WCC (15) comprises a metal tank with dimensions of roughly 100×50×50 cm, filled with distilled water. The interior volume of the detector can be viewed by four hemispherical photomultiplier tubes (PMT's) (16), each PMT being equipped with a photocathode with a diameter of 20 cm.

Upon the incidence of a gamma quantum of secondary radiation, for example from any of the reactions shown in equations (1), (2), or (3), into the sensing medium (water) of the WCC, one of photoelectric effect, Compton scattering, and electron-positron pair production may occur in the water inside the WCC. In the case of electron-positron pair production, the electrons and positrons are produced with corresponding energy spectra, the maximum values of which are close to the energies of the incident gamma quantum.

If the energy of an electron or a positron being propelled through water with a refractive index of n=1.33 exceeds 0.775 MeV, such a particle may generate Cherenkov radiation, which can be registered by a PMT. Thus, a water Cherenkov counter has a natural absolute energy threshold ≅0.8 MeV for registration of incident gamma quanta. In practice, taking into account the energy spectrum of the produced electrons and positrons, the effective value of this threshold is higher and closer to a value ≅2 MeV.

The operation of the secondary radiation WCC detector as shown in FIG. 2 may take place in the following manner. A starting generator (19) triggers an RTM-55 microtron (20) and sends pulses to a high-voltage PMT feed system (21) and a time analyzer (18). While the RTM-55 microtron (20) is triggered during the accelerator pulse, the PMT feed system (21) blocks the operation of the PMT's. At the end of an accelerator pulse, the time analyzer is initiated with the PMT's after a controlled delay of several milliseconds. The PMT signals generated upon recording the secondary radiation are processed by fast nanosecond electronics (17). In order to decrease the background load from noise signals on the PMT's, the logic of the fast electronics within the counter performs a selection of coincidences of signals from the PMT's with a plurality ≥2. The signals selected by the logic proceed to a "stop" input of the time analyzer (18), which is equipped with a histogram memory to accumulate the time spectrum of the PMT signals. After a given time (~15-20 ms) has passed, the time analyzer begins to accumulate the PMT signals, and the accumulated time spectrum from the histogram memory is entered into the computer (22) for further processing.

To further illustrate the operational capability of the device, according to an embodiment of the present disclosure, comprising a 55-MeV microtron and a WCC for detecting and measuring secondary radiation, computer modeling is performed. The computer modeling represents a use of a water-filled Cherenkov counter for the task of registering secondary radiation from a 100 g sample of trinitrotoluene (TNT) (see FIG. 6B for chemical structure) concealed by a 10-cm layer of water, from photonuclear reactions initiated by irradiation the TNT sample by a pulse of gamma radiation with a maximum energy of 55 MeV.

Figure 3:
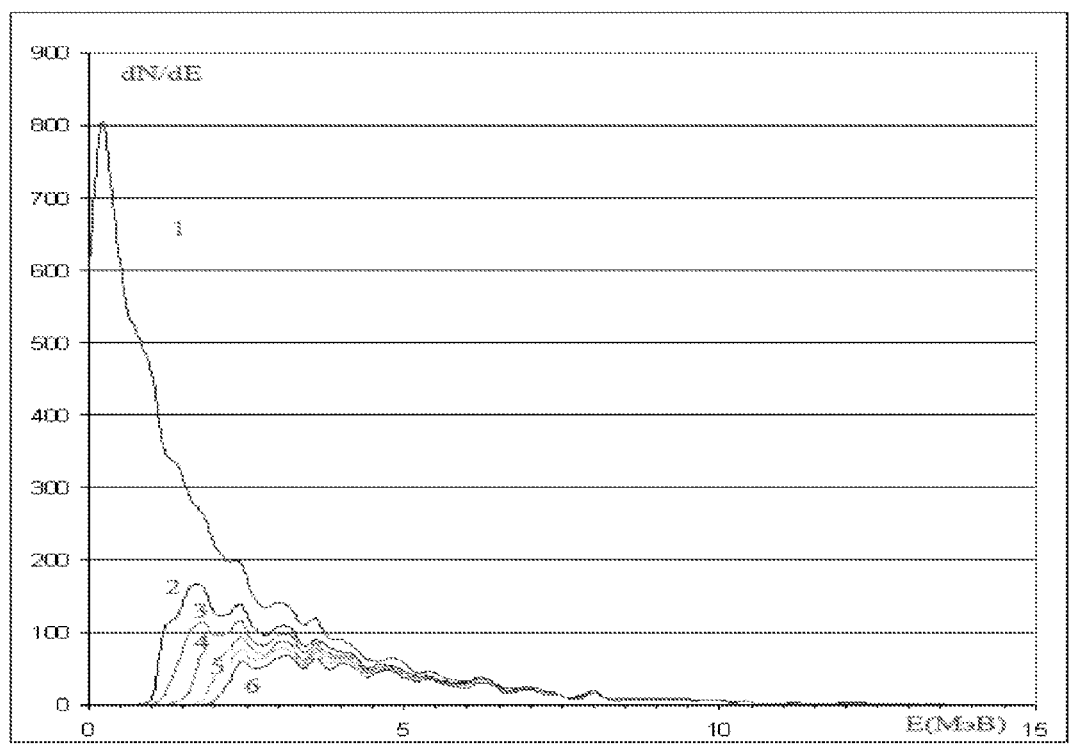
FIG. 3 shows a plot of modeled energy spectra of secondary gamma quanta incident on the WCC from a sample of trinitrotoluene.

FIG. 3 shows the modeled energy spectrum of the secondary gamma quanta incident on the WCC from the sample of TNT (Curve 1). Curves 2-6 of FIG. 3 correspond to dependencies of the number of events registered by the WCC as functions of the energy of the incident gamma quanta. Here each of the Curves 2-6 corresponds respectively to the cases where the PMT's and their electronics register events which generate more than 1, 25, 50, 75, and 100 photons of Cherenkov radiation.

Curve 1 of FIG. 3 shows that for recording events caused by one photon incident on a photocathode, a WCC can have an energy threshold of ≅0.8 MeV for registration of gamma quanta incident upon it. Curves 2-6 of FIG. 3 show that as the number of photons incident upon a photodiode increases from more than 1 to more than 100, the energy threshold for registration by a WCC increases to a value ≅2 MeV, while the efficiency of registration, decreases by only 2 times compared to the operating regime of a PMT with registration by individual photons.

Thus, the results of this computer modeling study of a water-filled Cherenkov counter (WCC) confirms the ability to effectively suppress, by natural filtering, the background signals which can be caused in a detector of carbon- and nitrogen-containing material (e.g. explosives and narcotics) by various electromagnetic processes that accompany irradiation of an object under inspection by a beam of primary gamma quanta.

Figure 4:
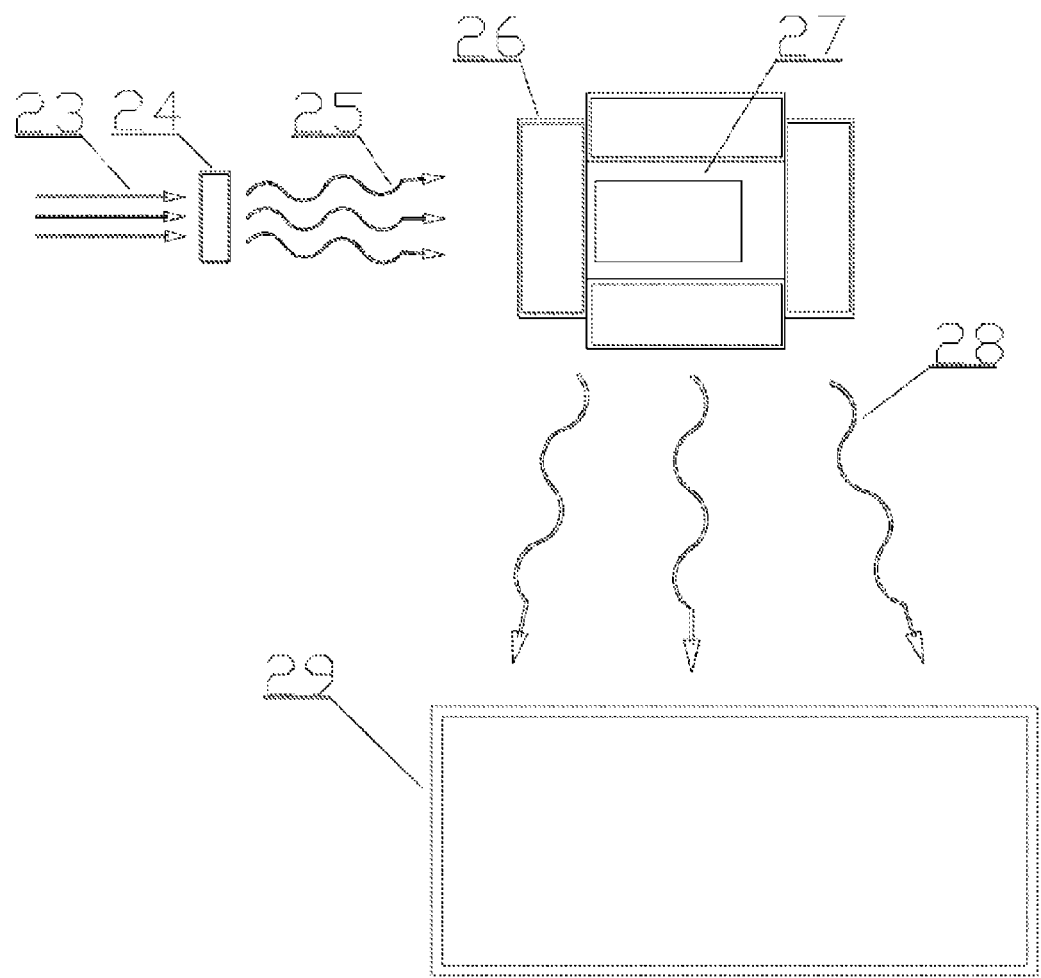
FIG. 4 shows a schematic of an exemplary physical embodiment of the device of the present disclosure comprising the microtron and the WCC.

To further illustrate the operational capability of the device, an experiment is performed with an exemplary physical embodiment of the device of the present disclosure, comprising a 55-MeV microtron and a WCC for detecting and measuring secondary radiation, to detect and identify concealed materials containing carbon and/or nitrogen. A schematic of a physical apparatus of the experiment is shown in FIG. 4. An electron beam (23) from an RTM-55 race-track microtron, as previously described in the present disclosure, with energy of 55 MeV, a pulse duration of 6 μsec, and a current of 10 mA is shown to be directed at a bremsstrahlung target (24) comprising a 0.3 mm thick tantalum plate. A beam of bremsstrahlung radiation (25) generated by the target (24) irradiated the test object (27), through a layer of concealment (26), represented by a layer of 6-cm-thick structural bricks. The secondary radiation (28) produced by the test object (27) upon irradiation by the bremsstrahlung radiation (25) is registered by a water-filled Cherenkov counter (WCC) (29) as described in the present disclosure.

An experiment with an exemplary physical embodiment of the device of the present disclosure is performed by initially measuring background emission with irradiation from the microtron by accumulating the time spectra while the brick container for the test object remained empty (a trial without the sample) after a controlled delay post irradiation from the microtron, and entering these spectra into the computer memory as a background data set.

Another measurement is made with a test object placed in the brick container and the same process of irradiation and accumulation of data repeated. The spectra are then stored into the computer memory as a test data set. The data sets stored into a computer memory can be processed in real time or subsequently off-line. In the experiment, the accelerator pulse repetition rate for the microtron is set at 10 Hz, and the length of time for accumulating the time spectrum is set at 80 ms for a single channel (bin) width of 1 ms.

The processing of the experimental data sets can begin with removing background signals from the recorded time spectrum. The background spectrum may be due to the influence of photoneutrons generated by the interaction of high-energy gamma quanta in the probe beam with the substance of the structural elements of the measuring system. The removal of background signals can be by a subtraction of the background data set of spectra collected without a sample from the data set of spectra collected with a sample. By this subtraction, background-compensated test data spectra can be obtained.

Figure 5:
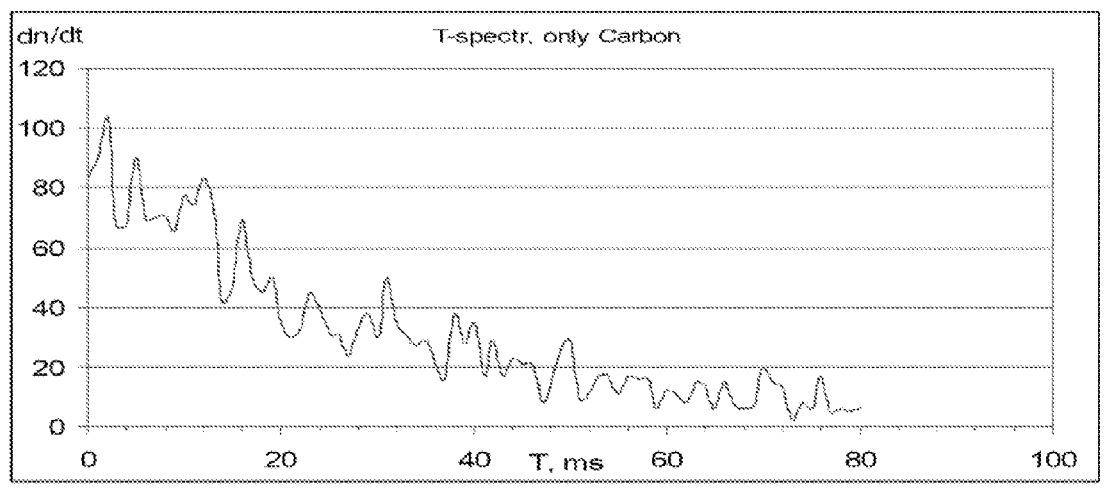
FIG. 5 shows a plot of an exemplary background compensated spectra for a graphite (carbon) sample.

Serving as test samples for detection and identification in the experiment are sample a) a plate of graphite (carbon), sample b) urea packing material (($NH_2$)$_2$CO), and sample c) materials which had no carbon and no nitrogen in their composition. For example, FIG. 5 shows the background compensated time spectrum of signals obtained in a trial with sample a), the plate of graphite for a single irradiation by a pulse of gamma radiation. Analysis of the obtained time spectrum performed by the technique described in Ref. [5] showed that the claimed device is able to detect and uniquely identify a substance containing nitrogen or carbon in less than 0.1 sec. The analysis method is described in more detail in Annex A. Thus, the above experimental and modeling examples demonstrate an operational capability and effectiveness of the device described in the present disclosure.

The examples set forth above are provided to give those of ordinary skill in the art a complete disclosure and description of how to make and use the embodiments of the present disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually, even if the citation refers to only the first page of the reference.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

REFERENCES

1. U.S. Pat. No. 4,756,866.
2. W. P. Trower: Imaging Carbon and Nitrogen Concentrations and the Interdiction of Concealed Narcotics and Explosives. Virginia Journal of Science, Vol. 44, No. 3, 1993.
3. E. A. Knapp, A. W. Saunders, and W. P. Trower: Direct Imaging of Explosives. Proceedings of MINE'99 Euroconference on: Sensor systems and signal processing techniques applied to the detection of mines and unexploded ordnance, Oct. 1-3, 1999. Villa Agape, Firenze, Italy; Laboratorio Ultrasuoni e Controlli Non Distruttivi, Universita di Firenze, Italy. http://demining.jrc.it/aris/events/mine99/start.htm
4. A device for discovery of concealed explosive materials. Russian Federation Patent No. 2185614. BI (Bulletin of Inventions) No. 20, 2002.
5. A method and device for discovery and identification of concealed explosive materials and narcotic substances. Russian Federation Patent No. 2226686, 2004.

The invention claimed is:

1. A device comprising:
an electron accelerator configured to generate pulses of an accelerated electron beam;
a breaking target configured to receive the pulses of the accelerated electron beam and generating an incident gamma radiation to be directed at a test object; and
a radiation detector configured to detect and measure secondary gamma radiation from carbon- and/or nitrogen-containing materials in the test object undergoing radioactive decay following irradiation of the test object by the incident gamma radiation, thus detecting and identifying the carbon- and/or nitrogen-containing materials in the test object,
wherein the radiation detector contains no carbon and/or no nitrogen in its sensing volume.

2. The device according to claim 1, further comprising control electronics, associated with the electron accelerator and the radiation detector, configured to:
initiate each of the electron accelerator pulses;
terminate each of the electron accelerator pulses;
time a controlled delay;
initiate measurements by photodetectors of the radiation detector only after the controlled delay after termination of each of the electron accelerator pulses; and
terminate measurements by the photodetectors before initiating the next electron accelerator pulse.

3. The device according to claim 1, wherein the electron accelerator is a race-track microtron.

4. The device according to claim 3, wherein the race-track microtron operates with an energy of 55 MeV and comprises an injection system, an accelerating structure, two reversing end magnets, a radiofrequency (RF) feed system, a beam diagnostic and steering system, and a control system.

5. The device according to claim 1, wherein the breaking target is tantalum.

6. The device according to claim 1, wherein the radiation detector has an energy threshold of about 0.8 MeV.

7. The device according to claim 1, wherein the radiation detector has an energy threshold of about 2 MeV.

8. The device according to claim 1, wherein the radiation detector is a water-filled Cherenkov radiation counter (WCC).

9. The device according to claim 1, wherein the detecting and identifying of the carbon- and/or nitrogen-containing materials in the test object comprises:
irradiating the test object by a pulse of gamma radiation, the test object comprising carbon- and/or nitrogen-containing material;
measuring of a secondary radiation from decay products of nitrogen-12 and boron-12 isotopes, wherein the nitrogen-12 and boron-12 isotopes are formed by the irradiation of the carbon- and/or nitrogen containing material from the test object;
recording one or more time spectra of signals from the secondary radiation; and
analyzing the spectra to determine if nitrogen-12 and/or boron-12 isotopes are present based on the decay signature thereof, thus detecting nitrogen- and/or carbon-containing materials.

10. The device according to claim 9, wherein the detecting and identifying of the carbon and/or nitrogen-containing materials in the test object further comprises comparing the relative content of nitrogen to carbon to a database of similar information based on known samples.

11. A device comprising:
an electron accelerator, comprising a race-track microtron with an operating energy of >50MeV and configured to generate pulses of an accelerated electron beam;
a breaking target, comprising tantalum and configured to receive the pulses of the accelerated electron beam and generating an incident gamma radiation to be directed at a test object; and
a radiation detector, comprising a water-filled Cherenkov radiation counter and configured to detect and measure secondary gamma radiation from carbon and/or nitrogen materials undergoing radioactive decay following irradiation of the test object by the incident gamma radiation, thus detecting and identifying the carbon and/or nitrogen containing materials in the test object.

12. The device of claim 11, wherein the water-filled Cherenkov radiation counter comprises:
a tank filled with water configured to interact with the secondary gamma radiation to generate Cherenkov radiation;
a plurality of photodetectors configured to measure the generated Cherenkov radiation in the tank filled with water; and
control electronics comprising a starting generator and a time analyzer and configured to:
initiate each of the electron accelerator pulses;
terminate each of the electron accelerator pulses;
time a controlled delay;
initiate measurements by photodetectors of the radiation detector only after the controlled delay after termination of each of the electron accelerator pulses; and
terminate measurements by the photodetectors before initiating the next electron accelerator pulse.

13. The device according to claim 12, wherein the Cherenkov radiation is generated by electrons and positrons formed by interaction of secondary radiation with water, the secondary radiation formed by radio-nuclei decay of boron-12 and nitrogen-12 formed by irradiation of a test object by gamma radiation from the breaking target bombarded by electrons accelerated by the race-track microtron.

14. The device according to claim 11, wherein wherein the device is adapted for detecting secondary gamma radiation from carbon and/or nitrogen containing materials in a test object concealed by one or more layers of concealment materials.

15. The device according to claim 11, wherein the device is adapted for detecting secondary gamma radiation from carbon and/or nitrogen containing materials concealed by one or more layers of concealment materials of a few millimeters to a few tens of centimeters thick each.

16. The device according to claim 11, wherein the device is adapted for identifying carbon and/or nitrogen containing materials in test objects concealed by one or more layers of concealment materials by identification of time spectra obtained by the irradiation of the test objects via a comparison of the time spectra of the test objects to the time spectra of known materials.

17. The device according to claim 11, wherein the device is configured for use in stationary or mobile installations.

18. The device according to claim 11, wherein the detecting and identifying of the carbon- and/or nitrogen-containing materials in the test object comprises:
irradiating the test object by a pulse of gamma radiation, the test object comprising carbon- and/or nitrogen- containing material;
measuring of a secondary radiation from decay products of nitrogen-12 and boron-12 isotopes, wherein the nitrogen-12 and boron-12 isotopes are formed by the irradiation of the carbon- and/or nitrogen containing material from the test object;
recording one or more time spectra of signals from the secondary radiation;
analyzing the spectra to determine if nitrogen-12 and/or boron-12 isotopes are present based on the decay signature thereof, thus detecting nitrogen- and/or carbon-containing materials.

* * * * *